(12) United States Patent
Limbach et al.

(10) Patent No.: US 11,498,057 B2
(45) Date of Patent: *Nov. 15, 2022

(54) HETEROGENEOUS CATALYST

(71) Applicants: Dow Global Technologies LLC, Midland, MI (US); Rohm and Haas Company, Collegeville, PA (US)

(72) Inventors: Kirk W. Limbach, Dresher, PA (US); Christopher D. Frick, Pottstown, PA (US); Dmitry A. Krapchetov, Landsdale, PA (US); Wen-Sheng Lee, Midland, MI (US); Victor J. Sussman, Midland, MI (US); Jeffrey A. Herron, Midland, MI (US)

(73) Assignees: Rohm and Haas Company, Collegeville, PA (US); Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/252,886

(22) PCT Filed: Jun. 20, 2019

(86) PCT No.: PCT/US2019/038154
§ 371 (c)(1),
(2) Date: Dec. 16, 2020

(87) PCT Pub. No.: WO2020/005693
PCT Pub. Date: Jan. 2, 2020

(65) Prior Publication Data
US 2021/0113997 A1    Apr. 22, 2021

Related U.S. Application Data

(60) Provisional application No. 62/691,128, filed on Jun. 28, 2018.

(51) Int. Cl.
| | | |
|---|---|---|
| *B01J 23/52* | (2006.01) | |
| *B01J 21/06* | (2006.01) | |
| *B01J 21/08* | (2006.01) | |
| *B01J 35/00* | (2006.01) | |
| *B01J 35/02* | (2006.01) | |
| *C07C 67/44* | (2006.01) | |

(52) U.S. Cl.
CPC ............ *B01J 23/52* (2013.01); *B01J 21/063* (2013.01); *B01J 21/08* (2013.01); *B01J 35/0073* (2013.01); *B01J 35/026* (2013.01); *C07C 67/44* (2013.01)

(58) Field of Classification Search
CPC ... B01J 23/10; B01J 23/52; B01J 23/44; B01J 35/008; B01J 35/023; B01J 21/04; B01J 21/06; B01J 21/08; B01J 21/10; B01J 21/12; B01J 21/14
See application file for complete search history.

(56) References Cited

U.S. PATENT DOCUMENTS

| | | |
|---|---|---|
| 4,249,019 A | 2/1981 | Tamura et al. |
| 4,518,796 A | 5/1985 | Aoshima et al. |
| 4,520,125 A | 5/1985 | Baer et al. |
| 5,969,178 A | 10/1999 | Okamoto et al. |
| 6,040,472 A | 3/2000 | Yamamatsu et al. |
| 6,228,800 B1 | 5/2001 | Yamaguchi et al. |
| 7,326,806 B2 | 2/2008 | Hayashi et al. |
| 8,461,373 B2 | 6/2013 | Suzuki et al. |
| 8,614,349 B2 | 12/2013 | Yokota et al. |
| 9,511,351 B2 | 12/2016 | Feaviour |
| 9,617,199 B2 | 4/2017 | Krill et al. |
| 2016/0280628 A1 | 9/2016 | Krill et al. |
| 2018/0001307 A1 | 1/2018 | Lygin et al. |
| 2018/0326400 A1 | 11/2018 | Lygin et al. |
| 2019/0084914 A1 | 3/2019 | Krill et al. |

FOREIGN PATENT DOCUMENTS

| | | |
|---|---|---|
| CN | 1931824 | 3/2007 |
| CN | 107519892 | 12/2017 |
| WO | 2009022544 | 2/2009 |
| WO | 2016113106 | 7/2016 |
| WO | 2017028905 | 2/2017 |
| WO | 2017084969 | 5/2017 |
| WO | 2019022887 | 1/2019 |
| WO | 2019057458 | 3/2019 |
| WO | 2019060192 | 3/2019 |
| WO | 2019139719 | 7/2019 |
| WO | 2019139720 | 7/2019 |

OTHER PUBLICATIONS

Parpeira et al., Nano-crystalline gold supported on Fe, Ti-silica support, (Applied Catalysis A: General 2011, p. 145-152, vol. 397).*

Nippon Catalytic Ltd (JP-2004181359 machine translation), Jul. 2, 2004.*

* cited by examiner

*Primary Examiner* — Jafar F Parsa
(74) *Attorney, Agent, or Firm* — Brian L. Mutschler

(57) ABSTRACT

A heterogeneous catalyst comprising a support and gold, wherein: (i) said support comprises titanium, (ii) said catalyst comprises from 0.1 to 5 wt % of gold, (iii) at least 90 wt % of the gold is in the outer 60% of catalyst volume, and (iv) particles of the catalyst have an average diameter from 200 microns to 30 mm; wherein weight percentages are based on weight of the catalyst.

10 Claims, No Drawings

HETEROGENEOUS CATALYST

BACKGROUND OF THE INVENTION

The invention relates to a heterogeneous catalyst. The catalyst is especially useful in a process for preparing methyl methacrylate from methacrolein and methanol.

Heterogeneous catalysts having noble metals supported on silica in combination with alumina and other elements are known, see e.g. U.S. Pat. No. 7,326,806B2. However, there is a need for additional catalyst particles with improved properties.

SUMMARY OF THE INVENTION

The present invention is directed to a heterogeneous catalyst comprising a support and gold, wherein: (i) said support comprises titanium, (ii) said catalyst comprises from 0.1 to 5 wt % of gold, (iii) at least 90 wt % of the gold is in the outer 60% of catalyst volume, and (iv) particles of the catalyst have an average diameter from 200 microns to 30 mm; wherein weight percentages are based on weight of the catalyst.

The present invention is further directed to a heterogeneous catalyst comprising a support and gold, wherein: (i) said support comprises silica and 0.1 to 90 wt % titanium, (ii) said catalyst comprises from 0.1 to 5 wt % of gold, and (iii) particles of the catalyst have an average diameter from 200 microns to 30 mm; wherein weight percentages are based on weight of the catalyst.

The present invention is further directed to a catalyst bed comprising particles of the heterogeneous catalyst.

The present invention is further directed to a method for preparing methyl methacrylate from methacrolein and methanol; said method comprising contacting a mixture comprising methacrolein, methanol and oxygen with a catalyst bed comprising particles of the heterogeneous catalyst.

DETAILED DESCRIPTION OF THE INVENTION

All percentage compositions are weight percentages (wt %), and all temperatures are in ° C., unless otherwise indicated. A "metal" is an element in groups 1 through 12 of the periodic table, excluding hydrogen, plus aluminum, gallium, indium, thallium, tin, lead and bismuth. "Titania" is titanium dioxide. Preferably, titanium is present as titania. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters.

Preferably the support has a surface area greater than 10 $m^2/g$, preferably greater than 30 $m^2/g$, preferably greater than 50 $m^2/g$, preferably greater than 100 $m^2/g$, preferably greater than 120 $m^2/g$. In portions of the catalyst which comprise little or no gold, the support may have a surface area of less than 50 $m^2/g$, preferably less than 20 $m^2/g$. Preferably, the catalyst particle which comprises silica comprises at least 0.1 wt % titanium, preferably at least 0.2 wt %, preferably at least 0.3 wt %, preferably at least 0.5 wt %; preferably no more than 85 wt %, preferably no more than 75 wt %, preferably no more than 65 wt %, preferably no more than 55 wt %, preferably no more than 45 wt %, preferably no more than 35 wt %, preferably no more than 25 wt %, preferably no more than 20 wt %, preferably no more than 15 wt %, preferably no more than 10 wt %, preferably no more than 5 wt %. Preferably, the catalyst particle is a silica particle comprising the aforementioned amounts of titanium. Preferably, the catalyst particle comprising titanum comprises from 50 to 100 wt % titanium; preferably at least 60 wt %, preferably at least 70 wt %, preferably at least 80 wt %, preferably at least 90 wt %, preferably at least 95 wt %. A catalyst support may also comprise alumina, magnesia, zirconia, boria, thoria, or mixtures thereof.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the particle include spheres, cylinders, rectangular solids, rings, multi-lobed shapes (e.g., cloverleaf cross section), shapes having multiple holes and "wagon wheels," preferably spheres. Irregular shapes may also be used.

Preferably, at least 90 wt % of the gold is in the outer 60% of catalyst volume (i.e., the volume of an average catalyst particle), preferably in the outer 50%, preferably in the outer 40%, preferably the outer 30%, preferably the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the gold is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the gold is within a distance from the surface that is no more than 15% of the catalyst diameter, preferably no more than 13%, preferably no more than 10%, preferably no more than 8%. Distance from the surface is measured along a line which is perpendicular to the surface.

Preferably, the average diameter of the catalyst particle is at least 300 microns, preferably at least 400 microns, preferably at least 500 microns, preferably at least 600 microns, preferably at least 700 microns, preferably at least 800 microns; preferably no more than 20 mm, preferably no more than 10 mm, preferably no more than 5 mm. The average diameter of the support and the average diameter of the final catalyst particle are not significantly different.

Preferably, the amount of gold as a percentage of the catalyst (gold and the support) is from 0.2 to 5 wt %, preferably at least 0.3 wt %, preferably at least 0.5 wt %, preferably at least 0.7 wt %, preferably at least 0.9 wt %; preferably no more than 4 wt %, preferably no more than 3 wt %, preferably no more than 2.5 wt %. Preferably, the catalyst comprises at least one third element selected from the alkali metals and alkaline earth metals, preferably magnesium. Preferably, the catalyst comprises from 0.1 to 10 wt % of third elements, preferably at least 0.2 wt %, preferably 3 wt %; preferably no more than 7 wt %, preferably no more than 5 wt %. Preferably, the catalyst comprises, in addition to the third element, at least one fourth element selected from cobalt and zinc. Preferably, the catalyst comprises from 0.1 to 10 wt % of fourth elements, preferably at least 0.2 wt %, preferably 0.5 wt %; preferably no more than 7 wt %, preferably no more than 5 wt %.

Titanium may be added to an existing silica support, or a cogel of silica and a titanium compound could be formed. In the case of adding titanium to an existing silica support, the titanium may be in the form of a salt placed in an aqueous solution. Preferably, the solution contains an acid such as nitric acid, sulfuric acid, hydrochloric acid, acetic acid or others. Preferably, the solution contains a sulfur-containing acid, e.g., thiomalic acid, preferably a carboxylic acid, e.g., citric or oxalic acid as well. Preferably, the sulfur-containing acid is present in a concentration of 1 to 10 wt % (preferably 3 to 8%). Preferably, the carboxylic acid is present in an amount from 0.1 to 25 wt % (preferably 0.5 to 15 wt %). Preferably, the weight ratio of sulfur to acid is 0.1:1 to 5:1, preferably from 0.2:1 to 3:1. Preferably, the support is washed with ammonium hydroxide prior to addition of gold precursor, preferably to remove chloride content to a level below 100 ppm in the bulk support, preferably below 50 ppm. The titanium compound may be in any form in which it subsequently will be precipitated onto the silica and preferably substantially converted to a titanium oxide, preferably titania (titanium dioxide) upon calcination. Suitable titanium compounds include, but are not limited to, nitrates, sulfates, oxyalates, alkyl titantates, and halides. Preferred titanium compounds are water-soluble, or if insoluble dissolved in an aqueous solution of acid in order to achieve solubility. Other titanium complexes that are water-soluble may also be utilized, such as dihydroxy bis(ammonium lactato)titanium(IV). Titanium compounds that dissolve in organic liquids such as alcohols could also be used, e.g., alkoxides. The titanium to silicon weight ratio is preferably 1 to 15 wt % titanium. Preferably, the support is produced by precipitating on a silica particle an aluminum salt. Preferably, the resulting material is then treated by calcination, reduction, or other treatments known to those skilled in the art to decompose the metal salts into metals or metal oxides. Preferably, the gold is precipitated from an aqueous solution of metal salts in the presence of the support. Preferred gold salts include tetrachloroauric acid, sodium aurothiosulfate, sodium aurothiomalate and gold hydroxide. In one preferred embodiment, the support is produced by an incipient wetness technique in which an aqueous solution of a titanium precursor salt is added to a silica particle such that the pores are filled with the solution and the water is then removed by drying. Preferably, the resulting material is then treated by calcination, reduction, or other treatments known to those skilled in the art to decompose the metal salts into metals or metal oxides. Preferably, gold is added to titania or a titanium-modified silica support by incipient wetness, followed by drying, and preferably by calcination.

Calcinations preferably are carried out at a temperature from 250° C. to 600° C.; preferably at least 300° C., preferably no more than 550° C. Preferably, the temperature is increased in a stepwise or continuous fashion to the ultimate calcination temperature.

In another preferred embodiment, the catalyst is produced by deposition precipitation in which a porous silica comprising titanium is immersed in an aqueous solution containing a suitable gold precursor salt and that salt is then made to interact with the surface of the inorganic oxide by adjusting the pH of the solution. The resulting treated solid is then recovered (e.g. by filtration) and then converted into a finished catalyst by calcination, reduction, or other treatments known to those skilled in the art to decompose the gold salts into metals or metal oxides.

The catalyst of this invention is useful in a process for producing methyl methacrylate (MMA) which comprises treating methacrolein with methanol in an oxidative esterification reactor (OER) containing a catalyst bed. The catalyst bed comprises the catalyst particles and is situated within the OER that fluid flow may occur through the catalyst bed. The catalyst particles in the catalyst bed typically are held in place by solid walls and by screens. In some configurations, the screens are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101.3 to 13890.8 kPa); preferably no more than 2000 kPa, preferably no more than 1500 kPa. Preferably, pH in the catalyst bed is from 4 to 10; preferably at least 4.5, preferably at least 5; preferably no greater than 9, preferably no greater than 8, preferably no greater than 7.5, preferably no greater than 7, preferably no greater than 6.5. Preferably, the catalyst bed is in a tubular continuous reactor.

The OER typically produces MMA, along with methacrylic acid and unreacted methanol. Preferably, methanol and methacrolein are fed to the reactor containing the fixed bed in a methanol:methacrolein molar ratio from 1:10 to 100:1, preferably from 1:2 to 20:1, preferably from 1:1 to 10:1. Preferably, the fixed bed further comprises inert materials. Preferred inert materials include, e.g., alumina, clay, glass, silica carbide and quartz. Preferably the inert materials are in the size range for the catalyst or smaller. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts.

EXAMPLES

Example #1

Single Pass Fixed Bed Bubble Column Reactor Operation:

A feed consisting of 20 wt % methacrolein, 200 ppm inhibitor, and a balance of methanol was fed at a rate of 40 g/hr to a ⅜" (9.5 mm) stainless steel tubular reactor containing a short front section of borosilicate glass beads followed by 5 g of catalyst. Catalyst #1 was utilized. A gas containing 8% oxygen in nitrogen was also feed to the reactor at a rate sufficient to obtain 4.5% O2 in the vent. The reactor was operated at 60° C. and 160 psig (1200 kPa). The product of the reactor was sent to a liquid-vapor separator and the vapor was sent to a condenser with liquid return and non-condensable gases going to the vent. Results are described in the below table.

Catalyst #1 Preparation:

Catalyst #1 was prepared by the incipient wetness technique using 20 g of Fuji Silysia Chemical, Ltd. CARiACT Q-10 support as the starting material and adding titanium to the support material. Specifically 10.5 g of titanium isopropoxide along with 3 g of glacial acetic acid were added in very small droplets to the catalyst in rotating equipment to ensure even distribution of the solution to the support material. The solution was at 40° C. when added. The modified support material was then dried under slight vacuum at 60° C. for 4 hrs and then calcined in air at ambient pressure by ramping the temperature at 5° C. per minute from ambient to 125° C., held for 1 hr and then ramped at 5° C. per minute up to 250° C. and held for 1 hr, then ramped at 5° C. per minute to 350° C. and held for 1 hr and finally ramped at 5° C. per minute to 450° C. and held for 4 hrs. Gold was then added to the support by incipient wetness technique utilizing 0.83 g of sodium aurothiosulfate in 10 g of deionized water at 40° C. The resulting catalyst was dried and calcined in air using the same heating profile as above. Analysis with a scanning electron microscope (SEM) equipped with energy-dispersive spectroscopy (EDS) of the catalyst clearly indicates that an eggshell deposition of both Ti and Au exists with the Au preferentially located only where Ti was deposited. The Ti and Au eggshell thickness was found to be approximately 50 microns or less. With an estimated loading of 10 mol % in the outer 50 microns of the 1 mm diameter catalyst, the local loading of titanium is estimated as up to 40 mol % as Ti/(Ti+Si).

Example #2

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" (4.2 mm) stainless steel tube maintained at 60° C. using an external heater. The reactor itself was packed with 2 mm glass beads to fill approximately 18 inches (45.7 cm) of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #2 Preparation:

Catalyst #2 was prepared by the following steps. First, a support material was prepared by impregnating magnesium nitrate hexahydrate to the incipient wetness point of 10 g of Fuji Silysia Chemical, Ltd. CARiACT Q-10 silica support material. The sample was then dried at 120° C. for 1 hr, followed by calcination at 450° C. for 4 hrs with a ramping rate of 5° C. per minute between different temperature settings. A quantity of 8.5 g of titanium isopropoxide and 1.5 g of acetic acid were mixed to provide a titanium precursor solution and 3.1 g of the titanium precursor solution was then impregnated to the above mentioned calcined Mg—SiO$_2$. The sample was then dried at 120° C. for 1 hr, followed by calcination at 550° C. for 6 hrs with a ramping rate of 5° C. per minute between different temperature settings. Gold deposition was achieved by impregnating a solution containing 0.3 g of sodium gold thiosulfate and 8 g of deionized water to the incipient wetness point of 8 g of the above described support material. The sample was then dried at 120° C. for 1 hr followed by calcination at 400° C. for 4 hrs. The resulting sample contained a total of 4.7 wt % Mg and 4 wt % Ti on Si with 1.5 wt % Au loaded on that material. The sample was not assessed to determine if eggshell deposition existed.

Example #3

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #3 Preparation:

Catalyst #3 was prepared by the following steps. First, a support material was prepared by Clariant Corporation utilizing a titanitium salt on Fuji Silysia Chemical, Ltd. CARiACT Q-10 silica support material. Gold deposition was achieved by impregnating a solution containing 0.39 g of sodium gold thiosulfate and 13.5 g of deionized water to the incipient wetness point of 10 g of the above described support material. The sample was then dried at 120° C. for 1 hr followed by calcination at 400° C. for 4 hrs.

Example #4 Comparative

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #4 Preparation:

Catalyst #4 was prepared by incipient wetness of 4.1 g sodium gold thiosulfate dissolved in 100 g of water to make an aqueous solution and then placed on 100 g of Fuji Silysia Chemical, Ltd. CARiACT Q-20C silica support material. The sample was dried at 120° C. for 1 hr followed by calcination at 400° C. for 4 hr. Gold loading was approximately uniform in the catalyst. This catalyst does not have an egg-shell gold loading.

Example #5

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #5 Preparation:

Catalyst #5 was prepared by incipient wetness of 0.1572 g of sodium aurothiomalate (I) with 3.0287 g DI water to make an aqueous solution and then placed on 5.0243 g titania spheres (Norpro) support material. The sample was dried at 120° C. for 1 hr followed by calcination at 300° C. for 4 hours with a temperature ramp of 5° C./min.

Example #6

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches (45.7 cm) of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #6 Preparation:

Catalyst #6 was prepared by incipient wetness of 4.1 g sodium gold thiosulfate dissolved, 0.4 g of mercaptosuccinic acid, and 0.12 g of citric acid monohydrate in 10 g of water to make an aqueous solution and then placed on 10 g of Fuji Silysia Chemical, Ltd. CARiACT Q-10 silica support material which had been previously treated to add approximately 6.6 wt % Ti, present as titanium oxide, to the support material. The catalyst was then placed inside a box oven with constant air purging of 50 liters per hour at room temperature for 1 hour and then the calcined at 400° C. with a temperature increase ramp of 5° C./min and a hold time at 400° C. of 4 hours.

| Catalyst # | Catalyst Description | Egg-shell Thickness (microns) | Volume Percent Egg-Shell (%) | STY (mol MMA/Kg cat-hr) | Aged Catalyst Au Nanoparticle Size (nm) | Normalized MMA Selectivity (%) |
|---|---|---|---|---|---|---|
| 1 | Au-Ti-Si | 50 | 27 | 4.9 | na | 98.4 |
| 2 | Au-Ti-Mg-Si | na | na | 5.5 | na | 98.9 |
| 3 | Au-Ti-Si | na | na | 7.5 | 5 | 99.5 |
| 4 comparative | Au-Si | na | na | 1.75 | 10 | 99.1 |
| 5 | Au-Ti | 115 | 20 | 5.2 | na | 98.0 |
| 6 | Au-Ti-Si | 130 | 34 | 4.2 | na | 99.9 |

1. The normalized MMA selectivity is the percent MMA among products originating as methacrolein reactant.
2. Distance from particle surface in which at least 50 wt % of Au is present (SEM/EDS).
3. Gold content of catalysts was approximately 1.5 wt %.
4. STY is the space time yield in mol MMA per Kg catalyst hour.

The TEM work was done at Dow Chemical using a FEI Themis field emission gun (FEG) transmission electron microscope (TEM). The TEM was operated at an accelerating voltage 200 keV. STEM images were collected at 1024×1024 or 2048×2048 image size. The Themis has Bruker AXS XFlash energy dispersive x-ray spectrometer (EDS) detector with an energy resolution of 137 eV/channel for elemental identification and quantitative analysis.

Catalyst 4, and other STEM images of fresh and aged catalysts have clearly indicated that gold nanoparticles are almost exclusively located in-between or in close proximity to titanium oxide particles which stabilize the gold nanoparticles, significantly decrease or for practical purposes eliminate the movement of the gold on the surface and thus significantly reduce the agglomeration and growth of these nanoparticles over time.

Rapid Aging Assessment Test

A rapid catalyst aging technique was developed to test the catalysts. In this technique, catalysts were aged at 200° C. in a solution of 4 wt % methacrylic acid, 6 wt % water and a balance of methanol for 10 days.

Catalyst 4 aged by this technique was compared with a 2 Kg sample of Catalyst 4 aged for 1600 hours in an adiabatic fixed bed reactor operated in recycle mode with air and liquid feed entering the bottom of the vertically aligned 2-inch OD (1.624-inch ID) {5.1 cm OD (4.1 cm ID)}×108 inch (274 cm) insulated 316SS reactor. The average temperature in this reactor was approximately 65° C. and the average pressure was approximately 160 psig. Fresh Catalyst 4 has an average gold nanoparticle size of approximately 4 nm. When the catalyst was aged at test conditions (200° C. in a solution of 4 wt % methacrylic acid, 6 wt % water and a balance of methanol for 10 days) the average gold nanoparticle size grew to approximately 10 nm. When the catalyst was aged in the 2 Kg reactor for 1600 hours, the average size also grew to 10 nm. Deactivation over this time frame in the 2 Kg reactor system is estimated to be approximately 15%. Catalyst aged by the test technique appears to have deactivated by approximately 20%.

The table below demonstrates the reduction in average gold nanoparticle growth which may be accomplished by the addition of Ti salts as well as those of 3' elements comprising an alkaline earth or rare earth metals (added to increase activity) and 4th elements consisting of Co, Zn, Bi, or Sb (added to further reduce gold nanoparticle size). For instance, Catalyst 3 and Catalyst 4 were aged under test conditions as described above. The gold nanoparticle size began at approximately 4 nm for both catalysts and grew to approximately 10 nm in the case of Catalyst 4 which was Au—Si versus approximately 5 nm in the case of Catalyst 3 which was Au—Ti—Si.

remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #7 Preparation:

Support material was prepared by incipient wetness 0.675 g of $C_4K_2O_9Ti*2H_2O$ dissolved in 9 g of water to make an aqueous solution and then placed on 10 g of Fuji Silysia Chemical, Ltd. CARiACT Q-10 silica support material. The support was then placed inside a box oven with constant air purging of 50 liters per hour at room temperature for 1 hour and then the calcined at 400° C. with a temperature increase ramp of 5° C./min and a hold time at 400° C. of 4 hours. The resulting support contained approximately 1.0 wt % Ti. Catalyst #7 was prepared by incipient wetness 0.385 g sodium gold thiosulfate dissolved in 8 g of water to make an aqueous solution and then placed on 10 g of Fuji Silysia Chemical, Ltd. CARiACT Q-10 silica support material which had been previously treated to add approximately 1.0 wt % Ti, present as titanium oxide, to the support material. The catalyst was then placed inside a box oven with constant air purging of 50 liters per hour at room temperature for 1 hour and then the calcined at 400° C. with a temperature increase ramp of 5° C./min and a hold time at 400° C. of 4 hours.

Example #8

Batch Recycle Fixed Bed Bubble Column Reactor Operation:

A feed solution of 150 g was prepared comprising 10 wt % methacrolein, 200 ppm inhibitor and a balance of metha-

| Cat. # | Catalyst Description | Ti (wt %) | Mg (wt %) | $4^{th}$ element (wt %) | Fresh/Aged Catalyst Au Nanoparticle Size (nm) | Fresh Catalyst STY (mol MMA/Kg cat-hr) | Normalized MMA Selectivity (%) |
|---|---|---|---|---|---|---|---|
| 3 | Au-Ti-Si | 6.6 | 0 | 0 | 4/5 | 7.5 | 99.5 |
| 4 comp. | Au-Si | 0 | 0 | 0 | 4/10 | 1.75 | 99.1 |
| 7 | Au-Ti-Si | 1 | 0 | 0 | 3.1/na | 4.3 | 99.9 |
| 8 | Au-Ti-Si | 3.3 | 0 | 0 | 3.4/na | 5.9 | 99.9 |
| 9 | Au-Ti-Zn-Mg-Si | 6.6 | 5 | 1 | 3.1/4.2 | 1.5 | 99.5 |
| 10 | Au-Ti-Zn-Mg-Si | 6.6 | 3 | 3 | 4/4 | 1.5 | 99.9 |
| 11 | Au-Ti-Co-Mg-Si | 6.6 | 5 | 1 | 2.8/3.5 | 2.2 | 99.9 |
| 12 | Au-Ti-Co-Mg-Si | 6.6 | 3 | 3 | 2.6/2.9 | 2.2 | 99.9 |

* The normalized MMA selectivity is the percent MMA among products originating as methacrolein reactant. STY is the space time yield in mol MMA produced per Kg catalyst hour. Gold loading on all samples was approximately 1.5 wt %.

Example #7

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The nol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #8 Preparation:

Catalyst #8 was prepared by incipient wetness 3.8 g sodium gold thiosulfate dissolved in 90 g of water to make an aqueous solution and then placed on 100 g of Fuji Silysia Chemical, Ltd. CARiACT Q-10 silica support material which had been previously treated to add approximately 3.3 wt % Ti, present as titanium oxide, to the support material. The catalyst was then placed inside a box oven with constant air purging of 50 liters per hour at room temperature for 1 hour and then the calcined at 400° C. with a temperature increase ramp of 5° C./min and a hold time at 400° C. of 4 hours.

Example #9

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #9 Preparation:

Support material was prepared by incipient wetness of 57.5 g Mg $(NO_3)_2*4H_2O$ dissolved in 100 g of water to make an aqueous solution and then placed on 100 g of Fuji Silysia Chemical, Ltd. CARiACT Q-10 silica support material which had been previously treated to add approximately 6.6 wt % Ti, present as titanium oxide, to the support material. The support was then placed inside a box oven with constant air purging of 50 liters per hour at room temperature for 1 hour and then the calcined at 400° C. with a temperature increase ramp of 5° C./min and a hold time at 400° C. of 4 hours.

Catalyst #9 was prepared by incipient wetness 0.268 g sodium gold thiosulfate and 0.24 g of zinc acetate dehydrate dissolved in 7 g of water to make an aqueous solution and then placed on 7 g of support material. The catalyst was then placed inside a box oven with constant air purging of 50 liters per hour at room temperature for 1 hour and then the calcined at 400° C. with a temperature increase ramp of 5° C./min and a hold time at 400° C. of 4 hours.

Example #10

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #10 Preparation:

Catalyst #10 was prepared by incipient wetness 3.8 g sodium gold thiosulfate dissolved in 90 g of water to make an aqueous solution and then placed on 100 g of Fuji Silysia Chemical, Ltd. CARiACT Q-10 silica support material which had been previously treated to add approximately 6.6 wt % Ti, present as titanium oxide, to the support material. The catalyst was then placed inside a box oven with constant air purging of 50 liters per hour at room temperature for 1 hour and then the calcined at 400° C. with a temperature increase ramp of 5° C./min and a hold time at 400° C. of 4 hours. 7.0 g of this Au—Ti—Si catalyst was then subjected to incipient wetness of 2.01 g of magnesium acetate tetrahydrate and 0.765 g zinc acetate dihydrate dissolved in 7 g of water. The resulting catalyst was then placed inside a box oven with constant air purging of 50 liters per hour at room temperature for 1 hour and then the calcined at 400° C. with a temperature increase ramp of 5° C./min and a hold time at 400° C. of 4 hours.

Example #11

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #11 Preparation:

Support material was prepared by incipient wetness of 57.5 g Mg $(NO_3)2*4 H_2O$ dissolved in 100 g of water to make an aqueous solution and then placed on 100 g of Fuji Silysia Chemical, Ltd. CARiACT Q-10 silica support material which had been previously treated to add approximately 6.6 wt % Ti, present as titanium oxide, to the support material. The support was then placed inside a box oven with constant air purging of 50 liters per hour at room temperature for 1 hour and then the calcined at 400° C. with a temperature increase ramp of 5° C./min and a hold time at 400° C. of 4 hours.

Catalyst #11 was prepared by incipient wetness 0.269 g sodium gold thiosulfate and 0.305 g of cobalt acetate tetrahydrate dissolved in 7 g of water to make an aqueous solution and then placed on 7 g of Fuji Silysia Chemical, Ltd. CARiACT Q-10 silica support material which had been previously treated to add approximately 6.6 wt % Ti, present as titanium oxide, to the support material. The catalyst was then placed inside a box oven with constant air purging of 50 liters per hour at room temperature for 1 hour and then the calcined at 400° C. with a temperature increase ramp of 5° C./min and a hold time at 400° C. of 4 hours.

Example #12

Batch Recycle Fixed Bed Bubble Column Reactor Operation:

A feed solution of 150 g was prepared comprising 10 wt % methacrolein, 200 ppm inhibitor and a balance of methanol, and placed in a 300 ml Parr® reactor which served as a gas disengagement vessel. The vessel liquid was maintained at a temperature of approximately 20° C. The liquid feed was pumped at 7 mL/min from the gas-disengagement vessel into the bottom of the vertically-oriented fixed bed reactor. Air and nitrogen gas was mixed to obtain 7.8 mol % oxygen and mixed with the liquid feed prior to entering the fixed bed reactor. The fixed bed reactor was a jacketed ¼" stainless steel tube maintained at 60° C. using an external heater. The reactor itself was packed with 2 mm glass beads to fill approximately 18 inches of the tube, then catalyst. The remaining void at the top of the reactor was filled with 3 mm glass beads. Liquid and gas exiting the top of the reactor were sent to a condenser and non-condensable gases were vented, while the liquid was recycled back into the gas-disengagement vessel.

Catalyst #12 Preparation:

Catalyst #12 was prepared by incipient wetness 3.8 g sodium gold thiosulfate dissolved in 90 g of water to make an aqueous solution and then placed on 100 g of Fuji Silysia Chemical, Ltd. CARiACT Q-10 silica support material which had been previously treated to add approximately 6.6 wt % Ti, present as titanium oxide, to the support material. The catalyst was then placed inside a box oven with constant air purging of 50 liters per hour at room temperature for 1 hour and then the calcined at 400° C. with a temperature increase ramp of 5° C./min and a hold time at 400° C. of 4 hours. 7.0 g of this Au—Ti—Si catalyst was then subjected to incipient wetness of 2.01 g of magnesium acetate tetrahydrate and 0.915 g of cobalt acetate tetrahydrate dissolved in 7 g of water. The resulting catalyst was then placed inside a box oven with constant air purging of 50 liters per hour at room temperature for 1 hour and then the calcined at 400° C. with a temperature increase ramp of 5° C./min and a hold time at 400° C. of 4 hours.

The invention claimed is:

1. A heterogeneous catalyst comprising a support and gold, wherein: (i) said support comprises titanium, (ii) said catalyst comprises from 0.1 to 5 wt % of gold, (iii) at least 90 wt % of the gold is in the outer 60 % of catalyst volume, and (iv) particles of the catalyst have an average diameter from 200 microns to 30 mm; wherein weight percentages are based on weight of the catalyst.

2. The catalyst of claim 1 in which particles of the catalyst have an average diameter from 300 microns to 20 mm.

3. The catalyst of claim 1 in which at least 95 wt % of the gold is in the outer 50% of catalyst volume.

4. A heterogeneous catalyst comprising a support and gold, wherein: (i) said support comprises silica and 0.1 to 90 wt % titanium, (ii) said catalyst comprises from 0.1 to 5 wt % of gold, and (iii) particles of the catalyst have an average diameter from 200 microns to 30 mm; wherein weight percentages are based on weight of the catalyst.

5. The catalyst of claim 4 in which at least 90 wt % of the gold is in the outer 60% of catalyst volume.

6. The catalyst of claim 4 in particles of the catalyst have an average diameter from 300 microns to 20 mm.

7. A method for preparing methyl methacrylate from methacrolein and methanol; said method comprising contacting a mixture comprising methacrolein, methanol and oxygen with a catalyst bed comprising the heterogeneous catalyst of claim 1.

8. The method of claim 7 in which particles of the catalyst have an average diameter from 300 microns to 20 mm and in which at least 95 wt % of the gold is in the outer 50% of catalyst volume.

9. A method for preparing methyl methacrylate from methacrolein and methanol; said method comprising contacting a mixture comprising methacrolein, methanol and oxygen with a catalyst bed comprising the heterogeneous catalyst of claim 4.

10. The method of claim 9 in which at least 90 wt % of the gold is in the outer 60% of catalyst volume and in which particles of the catalyst have an average diameter from 300 microns to 20 mm.

* * * * *